United States Patent [19]

Jansen et al.

[11] Patent Number: 4,906,469
[45] Date of Patent: Mar. 6, 1990

[54] APPROPRIATE CYTOTOXIC PHARMACEUTICAL COMBINATION ESPECIALLY FOR THE TREATMENT OF CANCERS

[75] Inventors: Franz Jansen, Saint Gely du Fesc; Pierrè Gros, Montpellier, both of France

[73] Assignee: Sanofi, Paris, France

[21] Appl. No.: 144,126

[22] Filed: Jan. 15, 1988

Related U.S. Application Data

[63] Continuation of Ser. No. 641,582, Aug. 17, 1984, abandoned.

[30] Foreign Application Priority Data

Aug. 23, 1983 [FR] France ................................. 83 13604

[51] Int. Cl.⁴ ...................... C12P 21/00; A61K 39/00; C07K 13/00
[52] U.S. Cl. ................................ 424/85.91; 435/70.21; 514/2; 514/8; 530/370; 530/387; 530/388; 530/389; 530/390; 530/391; 530/828
[58] Field of Search .............. 530/387, 390, 300, 381, 530/391, 377, 395, 428; 424/85.91; 514/2, 6, 8

[56] References Cited

U.S. PATENT DOCUMENTS 4,359,457 11/1982 Neville ............................. 421/85.91
4,450,154 5/1984 Masuho et al. ..................... 530/388

FOREIGN PATENT DOCUMENTS 2098730 11/1982 United Kingdom .................... 435/7

OTHER PUBLICATIONS

Wormsky et al., *Blood* vol. 57, pp. 657–662, 1981.
Battofora et al., *Cancer,* vol. 51, pp. 816–821 1983.

*Primary Examiner*—Robin Teskin
*Attorney, Agent, or Firm*—Bacon & Thomas

[57] ABSTRACT

The invention relates to a cytotoxic pharmaceutical combination comprising:
at least a first antibody possessing the capacity of selective recognition of a target antigen or antigens carried by cells to be destroyed, the said antibody being characteristic of an animal species different from that of the target cells,
at least one cytotoxic conjugate obtained by covalent bond coupling of the A chain of ricin with a second antibody specific for immunoglobins of the animal species to which the said first antibody or antibodies belong.

18 Claims, 1 Drawing Sheet

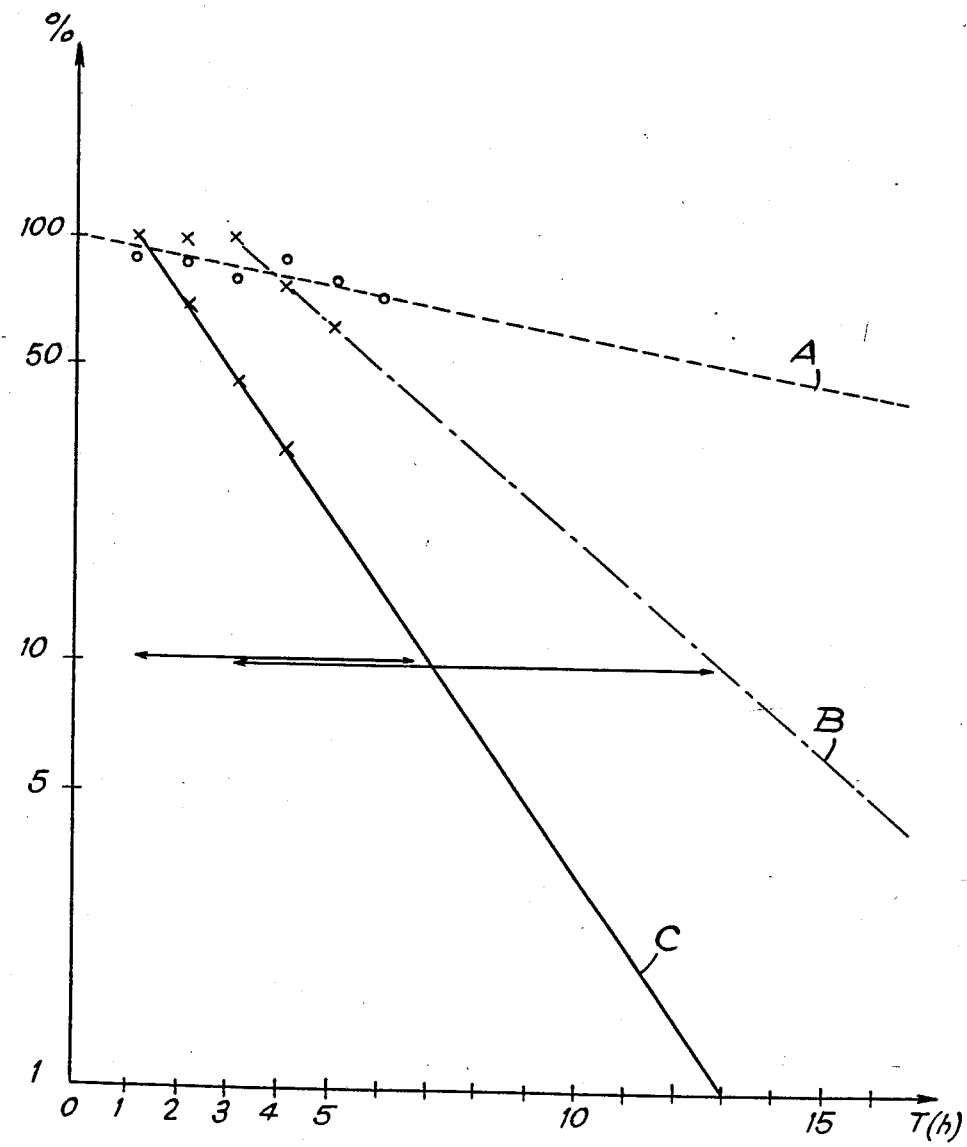

APPROPRIATE CYTOTOXIC PHARMACEUTICAL COMBINATION ESPECIALLY FOR THE TREATMENT OF CANCERS

This application is a continuation of application Ser. No. 641,582, filed Aug. 17, 1984, still pending.

In its earlier applications filed in France under No. 78/27838 of Sept. 28, 1978 and addition No. 79/24655 of Oct. 3, 1979, the applicant described the preparation of anticancer products called conjugates, or immunotoxins, obtained by covalent bond coupling of the A chain of ricin with a protein structure, such as an antibody, an immunoglobulin, or a fragment of immunoglobulin, capable of selectively recognizing a given antigen at the surface of the cells carrying this antigen to be targeted, such as cancer cells. The main property of these conjugates is their action as specific cytotoxic agents of the intended target cells.

The use of antibodies directed against haptenes, against differentiation antigens, or against antigens associated with cancer cells, already allowed the preparation of conjugates displaying remarkable specificity towards the target cells, and a very high cytotoxic power towards the same cells, as shown in the patent applications mentioned above, and also in subsequent applications No. 81/07596 and No. 81/21836 filed in France by the applicant.

The conjugates possessing these properties were always mixed artificial molecules in which the A chain of ricin was combined by a covalent bond of the disulfide type with an antibody, an immunoglobulin or a fragment of immunoglobulin, capable of selectively recognizing an antigen carried by the intended target cells.

Despite these remarkable properties of selective cytotoxicity possessed by these conjugates towards the cells bearing the antigen recognized by the antibody constituting said conjugates, it is evident, with products of this class, that it is necessary to prepare, to analyze at the chemical, biological and medical levels, and to produce for their use, as many different conjugates as the number of antibodies directed against different antigens, or even directed against different epitopes of the same antigen, capable of serving as a target for said conjugates on the different types of tumoral cell whose destruction is intended.

Continuing its research work in the field of selective cytotoxic conjugates, the applicant realized that this difficulty could be turned by using the products and processes, object of the present invention.

According to this invention, the mechanism of specific cytotoxicity implemented to achieve the selective destruction of the target cells comprises two steps in its logical aspect :

(a) In a first step, one or more antibodies or immunoglobulins or fragments of immunoglobulins are used, possessing the capacity of selective recognition of the target antigen or antigens that had been selected to characterize the cells to be destroyed.

In all cases, in this first step, the antibody or antibodies or immunoglobulins or fragments defined as indicated above and employed in their natural state, purified or not, without the need to couple them to any substance with cytotoxic properties, are used in the conditions enabling them to selectively bind themselves on the cells to be destroyed, and thus to make them identifiable for the subsequent step. If necessary, the antibody, not bound on cells, in excess, at least the major part of this excess, can be eliminated either by washing, or by any other suitable technique, such as filtration, centrifugation or any other technique of cell isolation or concentration.

(b) In a second step, use is made of at least one conjugate or hybrid molecule constructed by covalent bond coupling of the A chain of ricin with the second antibody or immunoglobulin or fragment of antibody or immunoglobulin or with a mixture of antibodies or immunoglobulins or fragments capable of selectively recognizing the first antibody or antibodies or immunoglobulins or fragments, as defined and used in the first step. The conjugate used in this second step is identical to the conjugates already described and claimed in the previous applications filed by the applicant and the previous patents granted to the applicant, except that the specificity selected for the antibody or antibodies used in the preparation of this or these conjugates does not imply the selective recognition of antigens present at the surface of the target cells, and especially of antigens associated with the tumoral state of the cells, but a specificity based on the criteria defined below. All the processes described by the applicant in its previous patents and patent applications are applicable to the preparation of the conjugates in the second step of the mechanism implemented by this invention.

In the following specification and in the claims, the term "antibody" is used to designate both antibodies and immunoglobulins and fragments of immunoglobulins.

The general methodology used to obtain the expression of a specific cytotoxicity, such as just described, comprises two steps in its logical aspect, which have been clearly distinguished to facilitate the understanding of the mechanism involved. In practice, according to the invention, the implementation of this mechanism may nevertheless take place:

either effectively in two steps, chronologically distinct, as described above, or by simultaneously using the first antibody or antibodies on the one hand, and the cytotoxic conjugate or conjugates on the other, all these products being placed in the presence of target cells in a single step, or by using complexes preformed between the first antibody or antibodies and the cytotoxic conjugate or conjugates, said complexes being prepared and, if necessary, purified before being placed in the presence of the target cells; the advantage of this process is to avoid both any excess of the first antibody or antibodies, any operation of elimination of this excess, and any excess of the cytotoxic conjugate or conjugates.

Although, in the latter case, the chronological order of implementation of the products is different from the one adopted in the previous disclosure, we shall continue in the rest of this text to designate by the expression "first antibodies" or "antibodies used in the first step" those whose specificity corresponds to the recognition of one or more antigens of the target The criteria selected to define the specificity of the antibody or antibodies used in the cytotoxic conjugate implemented in the second step are, according to the invention, fundamentally associated with the fact that the antibody or antibodies used in the first step are always one or mora antibodies characteristic of an animal species different from that of the target cells. Hence, as a result, it suffices for the antibody or antibodies constitutive of the cytotoxic conjugate to be specific for immunoglobulins of the animal species to which the antibody or antibodies used in the first step belong, in order that the cytotoxic conjugate binds itself only on the cells which, in the first step have already fixed the first antibody or antibodies. This species specificity criterion is generally sufficient if the antibody or antibodies of the conjugate are antibodies of a polyclonal nature. This also applies if the antibody or antibodies of the conjugate are polyclonal immunoglobulins, capable of recognizing all the immunoglobulins of the animal species to which the antibody or antibodies used in the first step belong. Alternative use can also be made of monoclonal immunoglobulins having the capacity to selectively recognize the class of immunoglobulins (A, D, E, G, M in particular) to which the first antibody or antibodies belong, as a function of the nature of the heavy chains constitutive of the immunoglobulins of this class in the determined species (for example, alpha, delta, epsilon, gamma or mu chains) or as a function of the nature of the light chains constitutive of the immunoglobulins in the determined species(- for example, kappa or lambda chains), or even having the capacity to selectively recognize the sub-class or sub-classes (or isotypes) of the first antibody or antibodies in the determined species.

Hence as a non-limitative example, if the first antibody is an immunoglobulin of Class G and isotype 2*a* of the mouse (IgG 2*a* of mouse) with a heavy chain of the gamma type and a light kappa chain applied to cells of human origin, the antibody used for the construction of the cytotoxic conjugate may be prepared from polyclonal or monoclonal immunoglobulins which are anti-total immunoglobulins of mouse mouse or anti-total IgG of mouse, or anti-gamma chains of mouse immunoglobulins, or anti-kappa chains of mouse immunoglobulins, or anti-IgG 2*a* of mouse, produced by specialized antibody-producing cells of any species suitable for this purpose.

A similar argument can be applied whatever the species, class, and possibly the isotype of the first antibody or antibodies used.

According to this invention, the antibodies or immunoglobulins or fragments of antibodies or immunoglobulins used either in the first step, or for the preparation of the cytotoxic conjugate used in the second step of the process, may equally be:

either of a polyclonal nature, if they originate in the blood of an animal previously immunized by conventional methods using an immunogen that carries the selected target antigen, or of a monoclonal nature, if they are produced by hybrid cells and especially by hybridomas, these hybrid cells themselves being obtained by fusing the splenic cells of an animal immunized against the selected antigen with cells of myeloma, for example, according to processes that are wellknown to the man skilled in the art; in this case, the immunization step may be performed either in vivo by suitable administration of the immunogen in the animal to be immunized, or in vitro by placing the splenic cells in direct contact with the immunogen (see in particular R. A. Luben, M. A. Mohlep, G. E. Nedwin, Clin. Invest., 64 (7) (1979). Moreover, the desired antibody may be obtained and purified or isolated, if necessary, either from supernatants of the culture of hybrid cells, or from the blood or the ascites fluid of animals inoculated with said hybrid cells.

It clearly appears, in such a system comprising two steps in its logic, that the total selectivity of the system is achieved by the antibody or antibodies used in the first step, which identify the carrier cells that carry the selected target antigens, and only them. The cytotoxic effect is due to the conjugate used in the second step, and this cytotoxic effect only concerns the cells which have fixed the first antibody or antibodies, due to the criteria stated above for the selection of the antibody or antibodies constitutive of the cytotoxic conjugate used in the second step.

Briefly, the general operation of this system is similar to that of the indirect immunofluorescence technique well-known to cytologists, with the difference that, in the invention, the second antibody carries the A chain of ricin as a powerful cytotoxic agent capable of killing the cells identified by the first antibody or antibodies, whereas, in the indirect immunofluorescence technique, the second antibody carries only a fluorescent compound which serves to display the cells identified by the first antibody.

A first advantage of such a system immediately appears, because it suffices to have only one or at most a small number of conjugates corresponding to the most frequent combinations of criteria of species, classes and isotypes indicated above, to make cytotoxic, in practically unlimited numbers, unmodified antibodies, directed against a very wide variety of membrane antigens of the cells to be destroyed. This property allows a considerable amplifying of the field of application of the cytotoxic conjugates resulting from the coupling of the A chain of ricin with an antibody.

A second advantageous property of these two-step systems is that they display properties of selective cytotoxicity that are perfectly identical and even sometimes superior to those of previously described systems comprising a single step. This analogy of behavior is confirmed at the level of the concentrations of the cytotoxic conjugate to be employed to achieve a predetermined cytotoxic effect (for example, 50% destruction of the population of the target cells) and also at the level of kinetics of cytotoxicity, namely of the time necessary for a predetermined fraction of the population of the target cells to be destroyed.

A third advantageous property of the two-step systems is that they can be potentialized by the same substances and in the same conditions as previously described systems comprising a single step. As a result, all the potentializing substances of immunotoxins already claimed by the applicant in its previous applications filed in France under Nos. 82/02091, 82/04119, 82/04047 and 82/04547 may also be used in the two-step systems, object of the present invention, with all the advantages related to cytotoxic effectiveness, kinetics and cytotoxicity, and specificity, which have already been demonstrated with the previously described immunotoxins.

A fourth advantage of the two-step system is that, with only one or a small number of cytotoxic conjugates employed in the second step, they make it possible to exploit the cumulative and simultaneous fixation, in the first step, of several unmodified antibodies on the same target cells. This is always reflected by a substantial gain in cytotoxic effectiveness, as demonstrated in the following illustrative examples. This property is especially valuable when the tumoral cells do not display, for any of the target antigens usable taken separately, densities of expression at the cell membrane that are sufficiently high for cytotoxic effectiveness to be satisfactory. In one-step systems, this difficulty can only be surmounted by simultaneously using several cytotoxic conjugates, each constructed with one antibody directed against one of the possible target antigens. However, this is reflected by an overall increase in the concentration of the cytotoxic products in the medium, incurring the risk of reaching a total concentration at which the side effects on non-target cells are no longer negligible. On the other hand, in a two-step system, it is possible to simultaneously or sequentially use several unmodified antibodies in the first step, each directed against one possible target antigen, making it possible to add the individual densities of these antigens. Since the non-specific toxicity of unmodified antigens is never a restricting factor in practice, and since, at any rate, the excess of these antibodies can be easily eliminated, the risks concerning non-target cells are negligible in this step. Subsequently, in the second step, a single cytotoxic conjugate can be used, in a concentration that is not different according to whether, in the first step, one or more unmodified antibodies were used. As a result, the risk of nonspecific toxicity is not increased in the second step.

Moreover, an additional advantage associated with the possibility of implementing several different antigens in two-step systems, carried in common by the target cells, without implying an increase in the risk of non-specific toxicity with respect to non-target cells, is to enhance the specific character of the cytotoxicity towards the target cells. Indeed, even if the antigens selected are not strictly specific of the population of the the target cells, but can also be individually expressed by the non-target cells, the probability that many of these antigens, if properly selected, are simultaneously present on the non-target cells, is very low, thus providing a powerful means to increase the selectivity of the cytotoxic system.

Finally, when in practice, two-step systems are used by observing the chronological separation between the two steps, and by proceeding with the elimination of the excess of the first antibody or antibodies, an additional advantageous property appears due to the fact that the first antibody or antibodies employed may be unpurified antibodies. Indeed, the procedure for eliminating the excess antibodies also eliminates all the other products constituting the impurities in the preparation. Hence, for example, serums of immunized animals, fractionated or not, supernatants of hybridoma culture, ascites fluids of animals inoculated with hybridoma cells, can be used directly without prior intensive purification.

The two-step selective cytotoxic systems described in this invention can be used in all situations in which selective cytotoxic conjugates or immunotoxins could already be used, operating in a single step. In addition, these two-step systems can be used jointly in each of these situations with any of the potentiation systems or potentiating products which have been previously described by the applicants. The main types of situation where use of such systems is specially valid are the following.

(a) Whenever a selective cytotoxic system or agent is useful in vitro for the specific destruction of a certain cell population in the presence of other cells to be preserved. Apart from many possible uses in the laboratory in research work, this situation is also encountered in the therapeutic field, particularly when such selective cytotoxic systems or agents are used to treat the bone marrow of cancer patients, and especially leukemia patients, in whom the marrow thus treated, in order to achieve a decrease or eradication of the tumoral cell population, is subsequently retransplanted (so-called autologous bone marrow transplantation protocol).

A similar situation occurs in the allogeneic medullary grafting protocols. In this case, the cell population to be selectively destroyed is not tumoral, but is represented by mature T lymphocytes of the donor, which are responsible in the recipient for the so-called graft-versus host disease if they are not eliminated in cases of incomplete histocompatibility between the donor and the recipient.

(b) Whenever a selective cytotoxic system or agent is useful in vivo as a therapeutic agent for the elimination of undesirable cells, especially tumoral, whether they belong to the primary tumor or to metastases.

The following examples offer a better understanding of the invention, without limiting its scope.

EXAMPLE 1

The cell model used in this example consists of cells of the CEM human lymphoblastoid line, originating in a T lymphoblastic leukemia, and uses three different target antigens, all three expressed by the same line, and which are the following:

antigen T-200, common to human leucocytes, recognized by the monoclonal antibody T 29-33 (see in particular H. Battofora and I. Towbridge, Cancer, 51, 816–821 (1983), antigen T-65, common to human T lymphocytes, recognized by monoclonal antibody T 101 (see in particular S. B. Wormsley, M. L. Collins and I. Royston, Blood, 57, 657–662 (1981), antigen of the HLA system, recognized by the monoclonal antibody MAS-015b (marketed by Sera Laboratories).

The unmodified monoclonal antibodies designated above are those that have been used, separately or in combination, in the first step of the two-step system.

In the second step, a single cytotoxic conjugate was used, obtained by covalent coupling using a disulfide bridge branch between the A chain of ricin on the one hand, and a preparation of anti-mouse IgG polyclonal immunoglobulins obtained in the sheep immunized by intradermal and intramuscular injections of pure mouse IgG and purified by affinity chromatography.

This cytotoxic conjugate was obtained by a technique similar to those described in our previous French applications No. 78-27838 and addition No. 79-24655, and Nos. 81-07596 and 81-21836, To do this, 11 ml of solution of purified sheep anti-mouse IgG immunoglobulin, or 50 mg of antibody, are added to 0.2 ml of the solution obtained by mixing 5 volumes of solution containing 20 mg/ml of (pyridyl-2 disulfanyl)-3 propionic acid in t-butanol and 1 volume of aqueous solution containing 60 mg/ml of ethyl-1(diethylamino-3 propyl)-3 carbodiimide. This mixture is incubated for 20 hours at 30° C. and dialysed continuously at 4° C. for 48 hours, against a total of 40 l of a phosphate buffer 0.125M, pH 7. After centrifugation, 11,5 ml of modified IgG solution containing 3.6 mg/ml are obtained, the modification rate being 3.0 dithiopyridyl groups introduced per mole of immunoglobulin. 11 ml of this activated antibody solution are mixed with 3.1 ml of a solution of the A chain of ricin (concentration 8.9 mg/ml). The mixture is incubated for 20 hours at 25° C., centrifuged and then chromatographed on a Sephadex G100 column, 2.6 cm in diameter, and 100 cm in height. The fractions corresponding to the molecules with molecular weight greater than or equal to 150,000 are collected and yield 57 ml of a solution of cytotoxic conjugate (or 33 mg) containing an average of 1.5 molecules of A chain of ricin coupled per molecule of immunoglobulin.

As a test, use was also made in these experiments of a cytotoxic conjugate with anti-T 65 specificity, identical to the one described in Example 1 of the previous French application No. 81-21836 filed by the applicant, and a cytotoxic conjugate with anti-T 200 specificity, constructed using antibody T29-33 in the same conditions of preparation as the anti-T 65 conjugate.

A CYTOTOXIC EFFECTIVENESS AND SPECIFICITY OF THE TWO-STEP SYSTEM

Six identical batches of CEM cells kept in RPMI 1640 medium containing 10% foetal calf serum (culture medium) at the rate of $5.10^5$ cells/ml are added respectively as indicated below:

batch 1 none
batch 2 antibody T29-33 (antiT200) to final 30 μg/ml
batch 3 antibody T101 (anti-T 65) to final 30 μg/ml
batch 4 antibody MAS-015b (anti-HLA) to final 30 μg/ml
batch 5 none
batch 6 none, and incubated for 2 hours at 4° C. After repeated washing three times at 4° C. using the culture medium, the cells of the six batches are placed in the presence of ammonium chloride in a final concentration of 10 mM (as potentiation). The anti-mouse IgG cytotoxic conjugate is added to the first four batches in the final concentration of $5.10^{-8}$M, expressed as the A chain of ricin.

Similarly, in the fifth and sixth batches, the anti-T65 and anti-T200 cytotoxic conjugates are respectively added in the same final concentrations of $5.10^{-8}$M expressed as the A chain of ricin.

From this stage on, the six batches of cells are incubated in the same conditions at 37° C. At different time intervals between 0 and 30 h after the placing in contact of the cells and the cytotoxic conjugate, aliquots belonging to each of the cell batches are subjected to the cytotoxicity measurement test. This test consists of measuring the capacity of the cells to incorporate $^{14}$C-leucine, according to a technique adapted to that described in J. of Biol. Chem. 249, 3557–3562 (1974). The determination of incorporated radioactivity is carried out hereon whole cells isolated by filtration. The incorporated radioactivity is calculated as a percentage of the value found for the control cells incubated in the same conditions, but in the absence of any cytotoxic agent. Brief Description of the FIGURE The results obtained are represented as a function of incubation time of the cells with the cytotoxic conjugate, in semilog coordinates, as shown in the FIGURE, which provides an example for batches 1, 3 and 5.

In this FIGURE, the incubation time in hours at 37° C. is plotted on the X axis and the percentage of cell protein synthesis in a logarithmic scale on the Y axis. Curves A, B and C correspond respectively to the following batches:

curve A batch 1, mouse-anti-IgG conjugate only
curve B batch 3, anti-T 65 antibody+anti-IgG conjugate only
curve C batch 5, anti-T 65 conjugate only.

Based on these results, one can also calculate the incubation time required for the residual tracer incorporation rate to be equal to one-tenth of the initial value of the control cells. This time, denoted by the symbol T10 and expressed in hours, appears in Table 1, which summarizes the overall experiment. It should be noted that these values of T10 are corrected for the duration of the initial latency period during which no inhibition of incorporation is detectable.

These results serve to draw the following conclusions.

With each of the three antibodies used in the first step (batches 2, 3 and 4), the two-step system leads to very high cytotoxicity, since, in all cases after 30 h, tracer incorporation is no longer detectable.

This cytotoxic effect strictly depends on the presence of the antibody used in the first step, because, in its absence (batch 1), the same anti-mouse innunoglobulin cytotoxic conjugate that has not found any target on the cells induces no cytotoxicity.

Whenever the cytotoxicity obtained by means of a cytotoxic conjugate used alone can be compared with the one obtained, thanks to the two-step system, implying the same antibody in the first step as the one used in the preparation of the previous cytotoxic conjugate, relatively similar kinetics are observed, indicating cytotoxic efficiencies of the same order of magnitude. However, it is interesting to note that, in one case (antigen T 65, comparison batch 3 versus batch 5), the two-step system is slightly less effective than the cytotoxic conjugate alone, whereas, for antigen T200 (comparison batch 2 versus batch 6), the two-step system is more effective than the cytotoxic conjugate alone.

B- VALUE OF USING SEVERAL ANTIBODIES IN THE FIRST STEP

In conditions totally identical to those described in Section A above, eight batches of CEM cells were used. Table 2 summarizes, for comparison with Table 1, the treatments applied to the eight batches employed. It appears that, in the first step of the two-step system, the three previously designated antibodies were used either separately, or in pairs (in the three possible combinations), or all three together. In all cases, each antibody was used in a concentration of 30 μg/ml, whether alone or combined with others, and the cytotoxic conjugate was employed in the final concentration of $5.10^{-8}$M expressed as the A chain of ricin, whatever the number of antibodies employed in the first step.

The cytotoxicity results expressed in T10 (in hours) are shown in Table 2, and serve to draw the following conclusions.

Batches 1, 2, 3 and 4, which are a repetition of the previous experiment, yield results perfectly consistent with those given in Table 1.

When the unmodified antibodies used in the first step are combined in pairs, a gain in cytotoxicity is observed in each case:

batch 5 versus batches 2 and 3: 6.5 h against 15 and 10 h,
batch 6 versus batches 3 and 4: 6.0 h against 10 and 6.7 h,
batch 7 versus batches 2 and 4: 5.3 h against 15 and 6.7 h.

When the unmodified antibodies are used all three together, the maximum cytotoxic effectiveness is obtained (T10=5 h).

These results very clearly show the acceleration of the kinetics of cytotoxicity that can be obtained when two or more membrane antigens are used simultaneously, without the need to increase the concentration of cytotoxic conjugate employed. This result is extremely important for all therapeutic applications in which one must obviously try to achieve the highest cytotoxic effectiveness possible, within the shortest period, and implementing the lowest possible concentration of cytotoxic conjugate.

As the results of the foregoing example clearly show, the products and processes described in this invention, when implemented for therapy, constitute a combination of active ingredients in which none of the active ingredients employed alone displays significant activity, whereas the combined use of representatives of each of the two classes of active ingredients concerned reveals a very high level of cytotoxic activity of therapeutic value.

According to the practical procedures of therapeutic use required, and depending on the precise indications of the treatment, the products described in the invention will be used in the form of drugs in two major types of possible presentation.

In the first type of presentation, the unmodified antibody or antibodies will be presented in the form of injectable solutions containing each antibody separately, or a mixture of the different antibodies to be used. Each unit bottle will contain preferably between 0.5 and 20 mg of each antibody in an aqueous, isotonic vehicle buffered to a pH preferably between 4 and 9. The packaging will allow either direct intravenous administration, introduction into an intravenous perfusion device, or introduction into receptacles containing the biological samples to be treated, particularly samples of bone marrow.

Moreover, this presentation will comprise the cytotoxic conjugate or conjugates in the form of injectable solutions containing each conjugate separately, or a mixture of the conjugates required. Each bottle will preferably contain 0.5 to 20 mg of each conjugate in a vehicle, and in a package similar to those described above.

The presentation of this first type allows maximum operating flexibility of the products of the invention, in so far as it allows the therapist complete freedom to employ the unmodified antibody or antibodies and the cytotoxic conjugate or conjugates in the ideal chronological order for the intended application.

In the presentation of the second type, the product or products to be used consist of injectable solutions containing the preformed soluble complex or complexes between the unmodified antibody or antibodies and the cytotoxic conjugate or conjugates. In these preparations, the constituents ensuring the formation of the complexes are present in a mole ratio preferably between 0.1 and 10, and selected in each specific case so that the preparation remains perfectly clear. The soluble complexes thus formed can be used as such, namely in the presence of an excess of the constituent that is not employed in complexation, or previously purified, for example by filtration on gel, to eliminate all or part of this excess. In all cases, these products are presented in unit bottles preferably containing 0.5 to 20 mg of useful product in a vehicle and a package similar to those described above.

TABLE 1

| batch No. | first step (unmodified antibody) | second step (cytotoxic conjugate) | T10 hours |
|---|---|---|---|
| 1 | — | anti-mouse IgG conjugate | ∞ |
| 2 | T 29–33 antibody | | |

TABLE 1-continued

| batch No. | first step (unmodified antibody) | second step (cytotoxic conjugate) | T10 hours |
|---|---|---|---|
|   | (anti-T200) | anti-mouse IgG conjugate | 6.5 |
| 3 | T 101 antibody (anti-T65) | mouse anti-IgG conjugate | 10 |
| 4 | MAS-015b antibody (anti-HLA) | mouse anti-IgG conjugate | 15 |
| 5 | — | anti-T65 conjugate | 6.0 |
| 6 | — | anti-T200 conjugate | 15 |

TABLE 2

| batch No. | first step (unmodified antibody | second step (cytotoxic conjugate | T10 (hours) |
|---|---|---|---|
| 1 | — | anti-mouse IgG conjugate | ∞ |
| 2 | anti-HLA | anti-mouse IgG conjugate | 15 |
| 3 | anti-T65 | anti-mouse IgG conjugate | 10 |
| 4 | anti-T200 | anti-mouse IgG conjugate | 6.7 |
| 5 | anti-T65 + anti-HLA | anti-mouse IgG conjugate | 6.5 |
| 6 | anti-T200 + anti-T65 | anti-mouse IgG conjugate | 6.0 |
| 7 | anti-T200 + anti-HLA | anti-mouse IgG conjugate | 5.3 |
| 8 | anti-HLA + anti-T65 + anti-T200 | mouse anti-IgG conjugate | 5.0 |

What is claimed:

1. A method for selectively destroying target cells carrying at least one antigen which comprises contacting the antigen carrying target cell with at least one first antibody or antibodies selective for at least one antigen on the target cells and which binds thereto, said first antibody being characteristic of an animal species different from that of the target cells, and contacting the antibody carrying target cells with at least one cytotoxic conjugate comprising the A chain of ricin covalently bound to an antibody specific for the immunoglobulins of the animal species to which the said first antibody belongs, in order to fix the cytotoxic conjugate to the first antibody or antibodies bound to the target cell so that the target cell is destroyed.

2. A method according to claim 1 which further comprises the elimination of excess of first antibody or antibodies prior to contacting the antibody carrying target cells with the cytotoxic conjugate.

3. A method according to claim 1, wherein the first antibody or antibodies and the cytotoxic conjugate are simultaneously brought into contact with the target cells.

4. A method according to claim 3, wherein the cells to be destroyed are tumoral cells.

5. A method for selectively destroying target cells carrying at least one antigen which comprises contacting the antigen carrying target cells with at least one preformed cytotoxic conjugate-antibody complex formed from at least one first antibody or antibodies which is selective for at least one antigen on the target cells and which binds thereto, the said first antibody being characteristic of an animal species different from that of the target cells, and at least one cytotoxic conjugate comprising the A chain of ricin covalently bound to an antibody specific for the immunoglobulins of the animal species to which said first antibody or antibodies belong in order to fix the cytotoxic conjugate-antibody complex to the target cell so that the target cell is destroyed.

6. A cytotoxic pharmaceutical composition for selectively destroying target cells carrying at least one antigen and comprising a cytotoxic effective amount of a complex formed from at least one first antibody or antibodies which is selective for at least one antigen on target cells and which binds thereto, the said first antibody being characteristic of an animal species different from that of the target cells, and at least one cytotoxic conjugate comprising the A chain of ricia covalently bound to an antibody specific for the immunoglobulins of the animal species to which the said first antibody or antibodies belong; and a pharmaceutically acceptable carrier.

7. A cytotoxic pharmaceutical composition according to claim 6 which is in the form of an injectable solution.

8. A cytotoxic pharmaceutical composition according to claim 6 wherein the first antibody is an anti-tumor cell antibody.

9. A cyotoxic pharmaceutical composition according to claim 8 wherein the antibody is anti-T 65, anti-T 200, anti-HLA or mixtures thereof, and the cytotoxic conjugate comprises the A chain of ricin covalently coupled to an antibody specific to immunoglobulin G.

10. A kit for selectively destroying target cells carrying at least one antigen which comprises, separately packaged, a pharmaceutical composition containing at least one first antibody or antibodies which is selective for at least one antigen on the target cells to be destroyed and which binds thereto, said first antibody being characteristic of an animal species different from that of the target cells; and separately packaged, a cytotoxic composition containing a cytotoxic effective amount for the target cells of at least one cytotoxic conjugate comprising the A chain of ricin covalently bound to an antibody specific for the immunoglobulins of the animal species to which the said first antibody or antibodies belong.

11. A kit according to claim 10, wherein the pharmaceutical compositions containing the antibody and the pharmaceutical composition containing the cytotoxic conjugate are each in the form of an injectable solution.

12. A kit according to claim 11, wherein each separately packaged composition represents a unit dose containing 0.5-20 mg of the antibody or the cytotoxic conjugate.

13. A cytotoxic pharmaceutical composition for selectively destroying target cells carrying at least one antigen which comprises at least one first antibody or antibodies which is selective for at least one antigen on the target cells and which binds thereto, said first antibody being characteristic of an animal species different from that of the target cells, and a cytotoxic effective amount of at least one cytotoxic conjugate comprising the A chain of ricin covalently bound to an antibody specific of the immunoglobulins of the animal species to which the said first antibody or antibodies belong and a pharmaceutically acceptable carrier.

14. A cytotoxic pharmaceutical composition according to claim 13 in the form of an injectable solution.

15. A cytotoxic pharmaceutical composition according to claim 14 wherein the antibody and cytotoxic conjugate are present in a mole ratio between 0.1 and 10.

16. A cytotoxic pharmaceutical composition according to claim 13 wherein the target cells are human cells, the said first antibody is derived from a mouse and the antibody portion of the cytotoxic conjugate is derived from a sheep and is specific to mouse immunoglobulin G.

17. A method according to claim 1 wherein the target cells are human cells, and said first antibody is derived from a mouse and the antibody portion of the cytotoxic conjugate is derived from a sheep and is specific of mouse immunoglobulins G.

18. A method according to claim 1 wherein the target cell is contacted with several different antibodies.

* * * * *